United States Patent [19]

Duce

[11] Patent Number: 5,098,548

[45] Date of Patent: Mar. 24, 1992

[54] HEATED SOLID ELECTROLYTE OXYGEN SENSOR

[75] Inventor: Richard W. Duce, Clio, Mich.

[73] Assignee: General Motors Corporation, Detroit, Mich.

[21] Appl. No.: 640,778

[22] Filed: Jan. 14, 1991

[51] Int. Cl.⁵ .............................................. G01N 27/26
[52] U.S. Cl. ...................................... 204/424; 204/427
[58] Field of Search ................................ 204/427, 424

[56] References Cited

U.S. PATENT DOCUMENTS

| | | | |
|---|---|---|---|
| 4,512,871 | 4/1985 | Kato et al. | 204/427 |
| 4,578,174 | 3/1986 | Kato et al. | 204/427 |
| 4,900,412 | 2/1990 | Ker et al. | 204/427 |

Primary Examiner—John Niebling
Assistant Examiner—Bruce F. Bell
Attorney, Agent, or Firm—Robert J. Wallace

[57] ABSTRACT

A self heating, readily assembleable solid electrolyte oxygen sensor is provided. A heater subassembly readily adaptable to unheated oxygen sensor technology, provides the means for positioning and rigidly securing the heater element within the oxygen sensing device through the use of locating means on the heater element and corresponding locating projections on the electric connector terminals. The terminals also provide the means for electrically coupling the resistance heating wires of the heater element to the external ground and power signals.

2 Claims, 3 Drawing Sheets

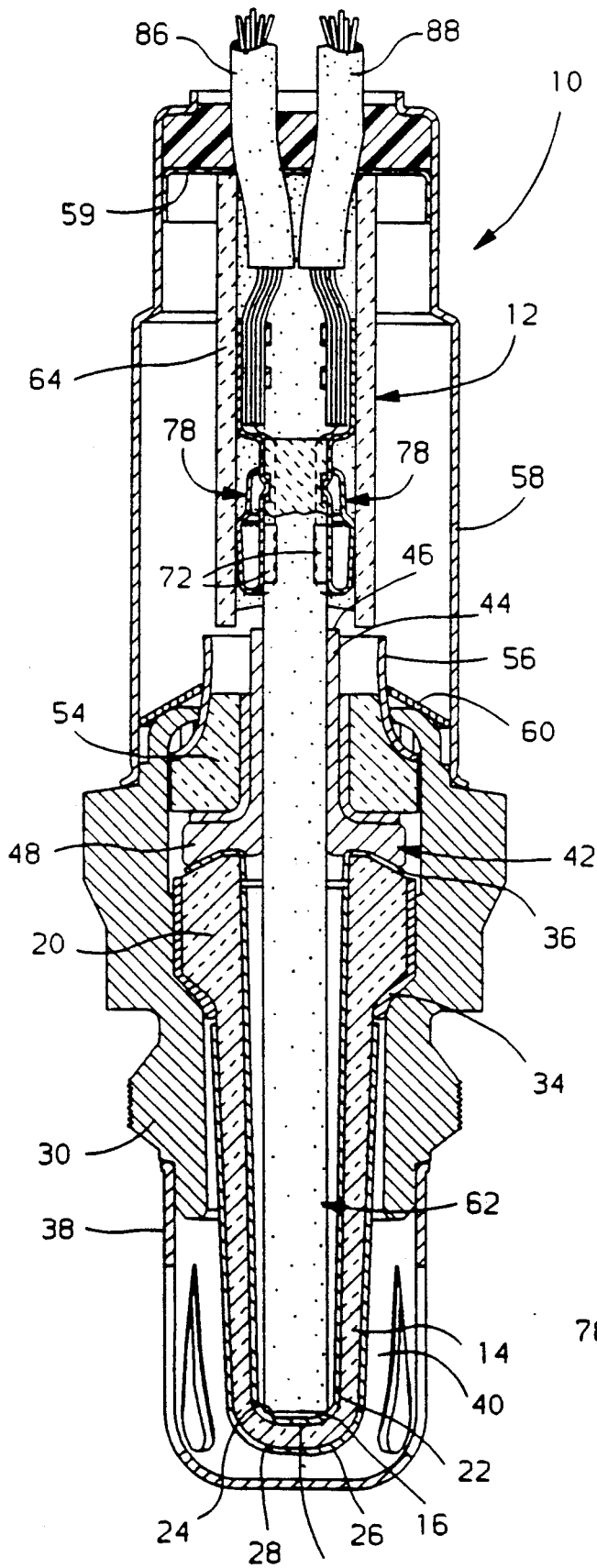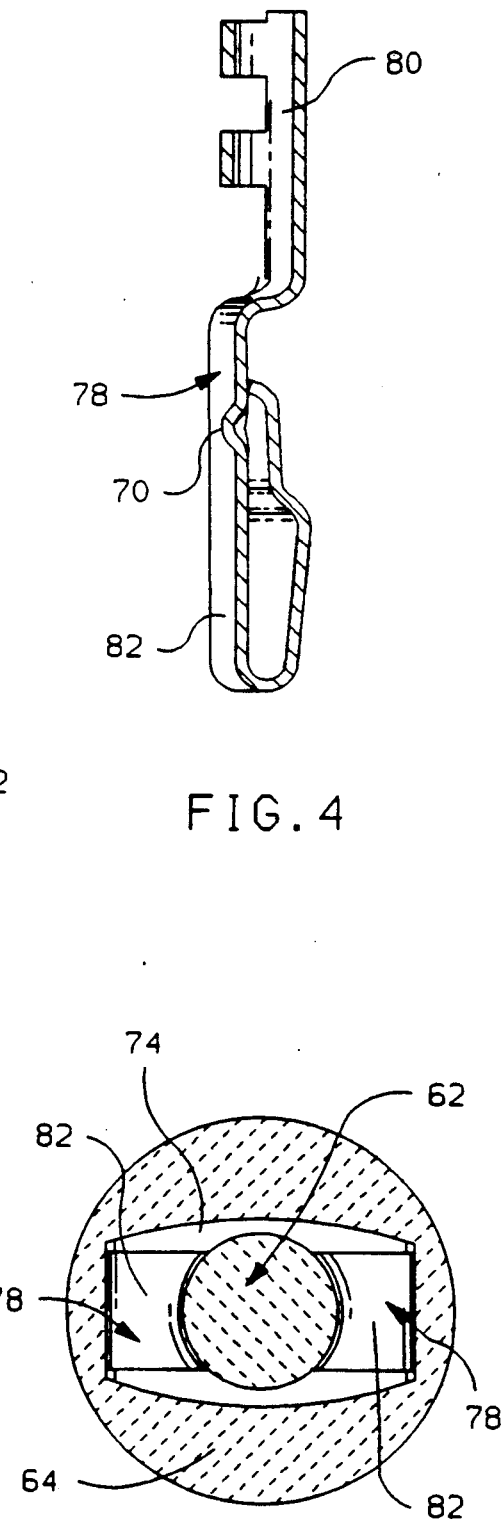
FIG. 1
FIG. 4
FIG. 6

HEATED SOLID ELECTROLYTE OXYGEN SENSOR

The present invention generally relates to an electrochemical type solid electrolyte oxygen sensor suitable for detecting oxygen concentrations in automotive exhaust emitted from an internal combustion engine. More specifically, this invention relates to a self heating oxygen sensor of this type which has a readily assembleable, leadless heater element.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Generally, the electrochemical type of oxygen sensor employed in automotive applications utilizes a thimble shaped electrochemical galvanic cell to determine, or sense, the relative amounts of oxygen present in the exhaust stream, an example being U.S. Pat. No. 3,844,920 to Burgett et al. This type of oxygen sensor is generally known and used throughout the automotive industry, and comprises an ionically conductive solid electrolyte material, typically yttria stabilized zirconia, a porous electrode coating on the exterior exposed to the exhaust or measuring gas and a porous electrode coating on the interior exposed to a known concentration of reference gas. The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant. Thus, the oxygen sensor senses the oxygen concentration in the exhaust gas by measuring this galvanic output voltage.

As evidenced by the above recitation of the Nernst equation, the galvanic output voltage of the sensor is dependent on temperature. In addition, the solid electrolyte member within such a sensor must first be heated to an elevated temperature in order to obtain an appreciable output voltage in response to the difference in the oxygen concentrations between the reference and measuring electrodes. The induced galvanic potential between electrodes and the corresponding output voltage are not stable until the solid electrolyte has been heated to a given temperature. In general, the conventional oxygen sensors which do not have means for self-heating, rely on the combustion gases to heat the solid electrolyte member of the oxygen sensor to an operating temperature sufficient to effect galvanic stability. Effective sensor operation is therefore delayed until the combustion gases reach an appropriate elevated temperature so as to thereby heat the solid electrolyte within the sensor to an appropriate operational temperature.

If the oxygen sensor is placed too far downstream in the exhaust pipe of an engine, especially a highly efficient engine, the sensor may not be heated to a high enough temperature during engine warm up to meet sensor specifications. During these conditions, the internal combustion engine control system operates open loop, i.e., the control system does not sense the controlled parameter—the air-to-fuel ratio—even though programmed to control that parameter. It is known that a large percentage of the total emissions produced during a short period of operation are produced during this period of engine warm up. In some applications, emissions control during engine warm up would be improved with an oxygen sensor which had means for rapidly heating itself to a predetermined temperature, regardless of the temperature of the surrounding environment.

Further, it is known that the temperatures of the combustion gases from an internal combustion engine vary widely during operation, up to about a few hundred degrees Centigrade. Therefore, another advantage of a self-heating oxygen sensor is that it may be positioned anywhere in the automobile exhaust pipe, even at the cooler exit end, since the solid electrolyte of the sensor is not dependent on the heat of the combustion gases for heating itself. By locating the heated oxygen sensor at the cooler exit end of the exhaust pipe, it is significantly less degrading to the physical and chemical properties of the sensor than being disposed at the hot end of the exhaust pipe.

In summary, there is a strong motivation to provide an oxygen sensor capable of heating itself. Many heated oxygen sensors have been previously proposed in the art. These prior heated oxygen sensors generally comprise an elongated ceramic heater which positively heats the solid electrolyte body of the sensor. The heater element is typically inserted into an elongated cylindrical hole formed in the solid electrolyte body. An example of a prior heated oxygen sensor of this type is United Stated Ser. No. 110,353 to Ker et al, entitled "Heated Solid Electrolyte Oxygen Sensor", which is assigned to the same assignee of this patent application.

However, there are difficulties associated with the assembly of such an elongated heater element within the oxygen sensor. It is necessary that the heater element be easily and precisely positioned, while rigidly secured within the sensor element. Further, for automotive applications particularly, a heated oxygen sensor should be rugged, reliable, and readily manufacturable at a low cost. Therefore, it is also desirable that the heater components be readily adaptable to the current oxygen sensor design and manufacturing techniques.

Therefore, what is needed is a heated oxygen sensor wherein the heater element is readily located and rigidly secured within the oxygen sensor. In addition, such a heater for this type of oxygen sensor should be amenable to automotive mass production techniques by being relatively simple in design, but also a rugged, reliable sensor assembly. Lastly, it is preferable that the heater element be readily incorporated into conventional unheated oxygen sensors typified by the above mentioned U.S. Pat. No. 3,844,920 to Burgett et al.

SUMMARY OF THE INVENTION

Accordingly, it is the primary object of the present invention to provide an improved heated solid electrolyte electrochemical oxygen sensor, the improved heated oxygen sensor being durable and reliable in operation even in widely varying temperature conditions.

It is a further object of this invention that such a heated oxygen sensor have a self aligning heater subassembly wherein the heater element is easily positioned and rigidly secured within the elongated bore of the solid electrolyte body, the heater subassembly also providing means for electrically communicating the electronic power signal to the heater element thereby eliminating the need for discrete electrical leads directly connected to the heater element.

It is still a further object of this invention that such a heated oxygen sensor be adaptable to conventional unheated oxygen sensor technology and readily amenable to automotive production techniques.

In accordance with the preferred embodiment of this invention, these and other objects and advantages are accomplished as follows.

According to the present invention, there is provided a heated oxygen sensing device suitable for detecting oxygen concentrations in automotive exhaust emitted from an internal combustion engine. The oxygen sensing device comprises a solid electrolyte body, a housing, an elongated heater element, and means for rigidly securing and centering the elongated heater element within the solid electrolyte body which also provides the power signal to the heater element.

The solid electrolyte body is substantially tubular and has an elongated bore located axially, with a first end closed by the solid electrolyte body and a second end open. A reference electrode is provided on the inner surface of the solid electrolyte body. A measuring electrode which contacts the exhaust gas to be measured is provided on the outer surface of the solid electrolyte body. The housing supports the solid electrolyte body so that the measuring electrode on the outer surface of the solid electrolyte body contacts the exhaust gas, while the reference electrode on the inner surface of the solid electrolyte body is gas tight to the external exhaust gas. The elongated heater element is inserted into the elongated bore within the solid electrolyte body. The heater element and solid electrolyte body are securely positioned so that a gap is provided substantially everywhere therebetween the solid electrolyte body and elongated heater element. The elongated heater element comprises a heating resistor having a positive temperature coefficient of resistance and a ceramic body carrying the heating resistor.

According to a preferred aspect of this invention, the elongated heater element has at its secured end, at least one locating means, which may be either a hole or an indentation for cooperating with at least one corresponding locating projection on at least one electrical connector terminal within the adapter. The secured end is the end of the heater element which is fixtured. In addition, the heater element has a corresponding number of electrically conductive pads for electrical contact with the electrical connector terminals which provide the ground and power signals to the heater element.

The adapter surrounds the electrical connector terminals and the top portion of the heater element at its securing end. A friction fit between the heater element and the terminals, and also between the terminals and the adapter, secures the heater element within the adapter. The locating projection on each terminal fits into the corresponding locating hole or indentation on the heater element, thereby precisely locating the heater element within the adapter and locking it into position so as to form a heater subassembly. The heater subassembly is then inserted into and self-aligned within the elongated bore of the solid electrolyte body.

In addition, the terminals electrically contact the electrically conductive pads on the heater element so as to provide the ground and power signals, thereby eliminating the requirement for separate electrical leads to the heater element. Electrical leads which would normally be necessary for electrical connection to the heater element are therefore not required with this invention.

With the use of this preferred embodiment, the heater element is rigidly secured and easily located within the solid electrolyte body. Further, with this invention, electrical leads which would normally be connected to the heater element are not required.

Other objects and advantages of this invention will be better appreciated from the following detailed description.

BRIEF DESCRIPTION OF THE DRAWINGS

The advantages of this invention will become more apparent from the following description taken in conjunction with the accompanying drawings wherein like references refer to like parts and wherein:

FIG. 1 is a cross-sectional view of a heated solid electrolyte oxygen sensor in accordance with a preferred embodiment of this invention and illustrates the solid electrolyte body, housing, heater element, adapter and connector terminals;

FIG. 4 is a side view of a terminal having a locating projection in accordance with a preferred embodiment of this invention;

FIG. 6 is a view of the heater subassembly shown in FIG. 2 along line 6—6 and illustrates the friction fit between the healer element, the terminals and the adapter.

DETAILED DESCRIPTION OF THE INVENTION

This invention provides a heated, solid electrolyte, electrochemical oxygen sensing device suitable for detecting oxygen partial pressures of exhaust gases emitted from an internal combustion engine, which is rugged, reliable, readily assembleable, and amenable to automotive production techniques.

Figures 2, 3:
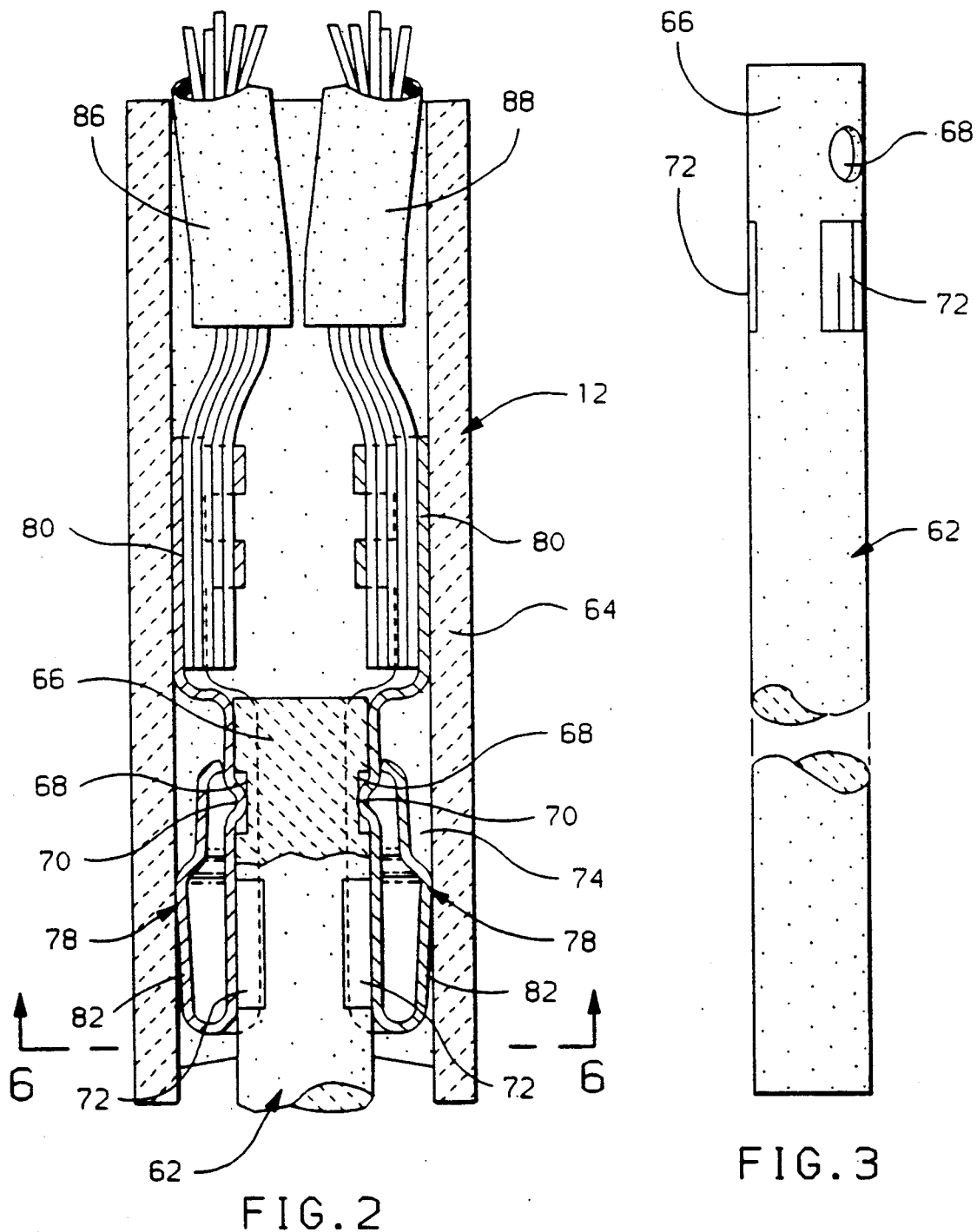
FIG. 2 is a partial cross-sectional view of the heater subassembly having the heater element located by and electrically contacting the connector terminals within the adapter in accordance with a preferred embodiment of this invention.
FIG. 3 is an elevational view of the heater element having locating means and electrical contact means in accordance with a preferred embodiment of this invention.

In the preferred embodiment of this invention, the heated oxygen sensing device 10, as shown in FIG. 1, comprises a heater subassembly 12, as shown more clearly in FIG. 2. Referring back to FIG. 1, the solid electrolyte body 14 comprises yttria stabilized zirconia and is substantially tubular having an elongated bore 16 located axially. The first end 18 of the solid electrolyte body 14 is closed by the solid electrolyte material. The second end 20 of the solid electrolyte body 14 is open, so that the heater subassembly 12 may be inserted into the elongated bore 16 of the solid electrolyte body 14. A reference electrode 22, preferably comprising porous platinum, is provided on the inner surface 24 of the solid electrolyte body 14 in the elongated bore 16 and contacts a known concentration of reference gas. A measuring electrode 26, preferably comprising porous platinum, is provided on the outer surface 28 of the solid electrolyte body 14 and contacts the exhaust gas to be measured.

The housing 30 is adapted to fit into the exhaust pipe of the automobile, typically by the use of a threaded mounting plate (not shown). The housing 30 supports the solid electrolyte body 14 so that the measuring electrode 26 on the outer surface 28 of the solid electrolyte body 14 contacts the external exhaust gas to be measured, while keeping the reference electrode 22 on the inner surface 24 of the solid electrolyte body 14 gas tight to the external exhaust gas. The solid electrolyte body 14 is mounted so as to resemble a finger-like projection into the flow of exhaust gases. Lower and intermediate electronically conductive gaskets 34 and 36, respectively, seal the elongated bore 16 of the solid electrolyte body 14 and prevent flow of the external exhaust gas into the elongated bore 16 of the solid electrolyte body 14 where the reference electrode 22 is provided. A perforated shield 38 is attached to the housing 30 and provides protection for the solid electrolyte body 14. A gap 40 is provided between the perforated shield 38 and solid electrolyte body 14 to allow uninterrupted flow of the exhaust gases through the perforated shield 38 to the porous platinum measuring electrode 26 on the outer surface 28 of the solid electrolyte body 14.

A hollow center terminal post 42 having a tubular extension 44 at an upper end 46 of the stop body 42 is concentric with the elongated bore 16 of the solid electrolyte body 14. The lower end 48 of the center terminal 42 is shaped to adapt to the intermediate gasket 36. The center terminal 42 may be formed from any suitable material, preferably a 400 series stainless steel. The center terminal 42 provides a self-aligning means for securely positioning the heater subassembly 12 during subsequent fabrication of the heated sensor 10.

An alumina insulator 54 is positioned above the metal center terminal post 42 and insulates it from the housing 30 and inner upper shield 56, which are both also preferably formed from a metal. In operation a galvanic output signal is generated between the reference and measuring electrodes 22 and 26. Electrical contact to measuring electrode 26 can be made through conductive seal 34 and the shell 30. Electrical contact to reference electrode 22 is made through conductive seal 36 to center terminal post 42. A wire (not shown) can be brazed to the upper end 44 of the center terminal post. The wire would extend upwardly inside outer upper shield 58, and exit outer upper shield 58, along side heater wires 86 and 88. The wire would then be connected to external measuring electronics (not shown). Therefore, the alumina insulator 54 is required to prevent electrical communication of this output signal to the housing 30 or inner upper shield 56.

Outer upper shield 58 is held by a spring clip 60, or other suitable means, to the inner upper shield 56. The outer upper shield 58 and inner upper shield 56 provide additional protection for the heated oxygen sensor 10 and may be formed from any suitable material.

FIG. 2 is a partial cross-sectional view of the heater subassembly 12 in accordance with a preferred embodiment of this invention. The heater subassembly 12, which is readily adaptable to conventional unheated oxygen sensor 10 design, as apparent from FIGS. 1 and 2, comprises an elongated heater element 62, an adapter 64 and electrical connector terminals 78 for providing the appropriate electrical signals to the heater element 62. An inventive feature of this invention resides in this heater subassembly 12.

The elongated heater element 62 is shown in FIG. 3. The heater element 62 is any commercial type of heater element having an alumina core with tungsten wires and an insulating overlayer, or may be conventionally formed. As an illustrative example, the heating resistors of the heater element 62 may be provided by thick film conductors which have been screen printed and patterned onto the ceramic base, preferably an alumina ceramic. The thick film heater element 62 utilizes a ceramic base material, such as alumina, with overlaying printed, electrically resistive heater ink (not shown). The ceramic base may be a single layer or a lamination of two or more layers. The green form of the ceramic base may be formed by roll compacting and pressing to produce an elongated bar having a circular cross-section. It is foreseeable that a heater element 62 having just about any desired cross-section could be used with appropriate modifications made to the adapter 64 (see FIGS. 1, 2, 5 and 6) and electrical connector terminals (see FIGS. 1, 2, 5 and 6) in accordance with the teachings of this invention.

The electrically resistive heating ink, which is preferably tungsten or platinum although other suitable materials such as palladium, silver or gold may also be used, is subsequently printed onto one side or both sides of the ceramic surface to form the heater element 62. Alternatively, the resistance heating ink may be printed on an underlying layer and subsequently covered by an overlaying layer of the ceramic, therefore sandwiched between intermediate layers of the ceramic base. Other suitable methods for depositing the resistance heating ink onto the ceramic base could also be used.

Figure 5:
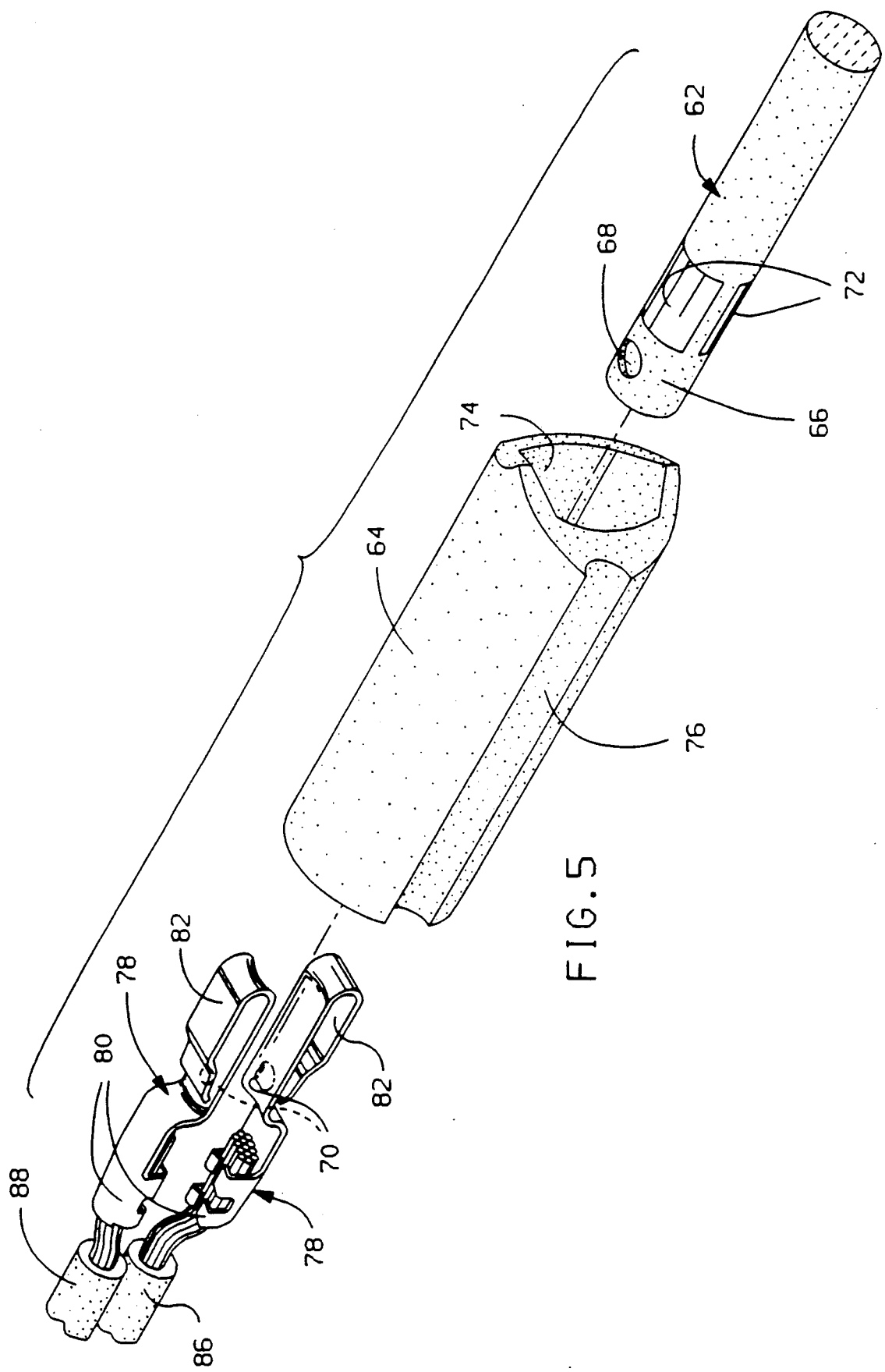
FIG. 5 is an exploded view of the heater subassembly in accordance with a preferred embodiment of this invention, illustrating the heater element, the adapter and the electrical connector terminals.

The resistance heating wires 86 and 88 (as shown in FIGS. 1, 2, and 5) which provide the power and ground signals within the heater element 62 and which are formed by the electrically resistive ink are preferably patterned so as to be provided primarily in that region of the heater element 62 which will subsequently be inserted into the closed end 18 of the solid electrolyte body 14 in the region where the solid electrolyte body 14 contacts the exhaust gases to be measured. The resistance heating wires may be provided throughout the entire length of the heater element 62, however it is preferable that they be primarily located, such as by the use of a serpentine-like pattern to maximize the heat generated, in the region where heating is desirable. Generally, this is only the region which extends into that portion of the solid electrolyte body 14 which contacts the exhaust gases to be measured; i.e., approximately the last 20 percent of the heater element 62. Therefore, only the necessary regions of the sensor 10 are heated, thereby avoiding the heating of any unnecessary components or unduly massive components which would be required for adequate heat transfer and thermal stress relief.

In addition, it is preferred that the resistance heating material of the heater element 62 have a positive thermal coefficient of resistance. Therefore, as the temperature of the heater element 62 is increased, it becomes increasingly more difficult to raise the temperature of the heater element 62, thereby allowing the exhaust gases to naturally heat the element 62 and sensor 10. A positive thermal coefficient of resistance of about 0.3 %/° C. is appropriate, although the coefficient may vary between about 0.1-0.5 %/° C. without significant detrimental effects to the sensor 10.

According to a preferred aspect of this invention, shown in FIG. 3 most clearly, the elongated heater element 62 has at its secured end 66, at least one locating means 68. Preferably, the locating means 68 is a hole within the heater element 62, however an indentation of sufficient depth may also be utilized. The locating means 68 on the heater element 62 corresponds to and cooperates with a locating projection 70 (shown in FIG. 4) on an electrical terminal 78 of the adapter 64. Within the heater element 62, a hole 68 (see FIG. 3 and 5) is preferred as the locating means, since it ensures precise location with the locating projection 70 on the terminal 78, and more rigid retention than if only an indentation were used as the locating means 68. In addition, it is desirable that there be the same number of locating means 68 on the heater element 62 as there are number of electrical conductor terminals 78 in the adapter 64, so as to maximize the benefits of this invention. There will most likely always be at least two electrical conductor terminals 78 since these would correspond to the electrical connections to the power and ground wires 86 and 88 respectively. However there may be more terminals, and even foreseeably only one terminal, if such applications were desired.

In addition, the heater element 62 has a corresponding number of electrically conductive pads 72, as shown clearly in FIG. 3, for electrical contact with the corresponding electrical conductor terminals 78 (see FIGS. 2 and 5). The electrically conductive pad 72 is formed by depositing a suitable electrically conductive layer of metal onto the heater element 62. Preferably, a layer of gold is plated onto the heater element 62 in those regions which will contact the electrical conductor terminal 78, although other suitable materials may also be used. The electrically conductive pads 72 are electrically connected to the resistance heating wires within the heater element 62. Therefore, when the electrical connector terminals 78 within the adapter 64 contact these electrically conductive pads 72, the electrical power and ground signals (represented by 86 and 88 respectively) are communicated to the resistance heating wires within the heater element 62, without bonding the electrical leads directly to the ceramic heater element 62. This is a desirable feature of this invention.

A side view of an electrical terminal 78 in accordance with a preferred embodiment of this invention is shown in FIG. 4. The connecting end 80 is adapted for conventional electrical connection to a signal wire (not shown). In the preferred embodiment (shown in FIGS. 1, 2 and 5), the terminals 78 are electrically connected to the power and ground signal wires 86 and 88 respectively, for connection to the heater element 62. About midway along the length of the terminal 78 is the locating projection 70 which corresponds to the locating hole 68 on the heater element 62. The locating projection 70 is diametrically matched to the locating hole 68 on the heater element 62 so that preferably there is a friction fit between the locating hole 68 and the locating projection 70, so as to prevent rotation of the heater element 62 after assembly and to ensure rigid retention of the heater element 62. The locating projection 70 is made to be sufficiently thick to ensure a good fit with the locating means 68 of the heater element 62, therefore it is about equal to the thickness of the terminal 78. However manufacturing practicability of the locating projection 70 must also be considered.

The opposite end of the terminal 78 from the connecting end 80 is the contacting end 82, which contacts the gold contact pad 72 on the heater element 62 to electrically communicate the desired signal to the heater element 62 (shown in FIG. 2). It is apparent that the terminal 78 must be formed from an electrically conductive material, such as copper or other appropriate material. The contact end 82 is formed with a reverse bend so as to provide a biased friction fit between the terminals 78 and the adapter 64 after assembly. The number of terminals 78 is dependent upon, and the same as, the number of connectors required for the particular application. In the preferred embodiment there are two connectors, a ground and a power wire (86 and 88 respectively), however there may also be applications where more connectors are desired, such as where a redundant signal is required.

FIG. 5 is an exploded view of the heater subassembly 12 shown in FIG. 2. The adapter 64 is designed to be a relatively simple shape, therefore it is easy to manufacture at a low cost. It is formed from an electrically insulative material to prevent unnecessary shorting of the various electrical signals, as an example it could be formed from an appropriate ceramic like alumina. The adapter 64 is generally tubular shaped, however in cross-section, its outer periphery need not be circular. It can be any convenient configuration, including rectangular. The inner opening 74 is not circular in cross-section. A cross-section of this inner opening 74 preferably resembles generally a barrel shape. This type of shape is necessary to accommodate and rigidly fixture the electrical conductor terminals 78 and the heater element 62. The outside perimeter of the adapter 64 is preferably circular in this example, to facilitate the manufacturability. Optionally, a relief groove 76 (shown in FIG. 2) may be formed along the length of the adapter 64 for carrying the signal wire from center terminal post 42 if there is insufficient room on upper outer shield 58 (shown in FIG. 1) to accommodate it.

As depicted in FIG. 5, the heater element 62 is inserted within the adapter 64, and the electrical connector terminals 78 are inserted between the heater and the adapter 64. As shown in FIG. 2, the terminals 78, which are conventionally connected to the electrical power and ground connectors 86 and 88, retain the heater element 62 at its secured end 66, by means of a friction fit between the heater element 62 and the terminals 78. The locating projection 70 on each terminal 78 fits into the corresponding locating hole 68 or indentation on the heater element 62, thereby precisely locating the heater element 62 and locking it into position. A locating hole 68, instead of an indentation, is preferred so as to maximize the locateability and the retention by the terminals 78. The terminals 78 are also held within the adapter 64 by means of a friction fit at both the connecting end 80 and the contact end 82 of each terminal 78. However, a friction fit between the connecting ends 80 and the adapter is not necessary. The friction fit between the heater element 62, the terminals 78 and the adapter 64 is shown in FIG. 6 which is a cross-sectional view alone line 6—6 of FIG. 2. With this invention, the heater element 62 and terminals 78 are rigidly secured within the adapter 64 so as to form the heater subassembly 12.

The heater element 62 is positioned by the terminals 78 within the adapter 64 so that an appropriate length of the heater element 62 projects into the elongated bore 16 of the solid electrolyte body 14 when the heater subassembly 12 is inserted into the elongated bore 16 of the solid electrolyte body 14 (as shown in FIG. 1). The heater length and adapter length are coordinated to allow the heater lower end to abut the lower end 18 of solid electrolyte body 14, or more specifically the reference electrode 22 covering that end. The upper end of adapter 64 engages the upper end wall 59 of upper outer shield 58, or at least closely approaches it. In such an arrangement, heater 62 may not have to be rigidly supported by center terminal post 42.

A desirable feature of the present invention is its amenability to automotive mass production techniques. The heater subassembly 12 is relatively easy to assemble and may be utilized in conventional unheated oxygen sensors without much modification of the conventional design. The heater subassembly 12 when installed is essentially self locating and rigidly secured in all directions of movement. Further the heater subassembly 12, particularly the electrical connector terminals 78, provide the means for electrically communicating the necessary signals to the heater element 62, therefore substantially simplifying the design of the heater element 62.

While our invention has been described in terms of a preferred embodiment, it is apparent that other forms could be adopted by one skilled in the art, such as by modifying the number of electrical connector terminals, modifying the materials of the various components, modifying the shape of the locating means, or by providing the locating projection on the heater element and the locating hole on the terminal. Accordingly, the scope of our invention is to be limited only by the following claims.

The embodiments of the invention in which an exclusive property or privilege is claimed are defined as follows:

1. An oxygen sensing device, comprising: a substantially tubular solid electrolyte body having an elongated bore axially located, with a first end closed by said solid electrolyte and a second end open, said solid electrolyte body having a reference electrode provided on an inner surface thereof and a measuring electrode provided on an outer surface thereof;

a housing, said housing supports said solid electrolyte body so that said measuring electrode of said solid electrolyte body contacts the external gas to be measured and so that said reference electrode of said solid electrolyte body is gas tight to the external gas to be measured;

an elongated heater element comprising a heating resistor having a positive coefficient of resistance and a first end inserted within said elongated bore of said solid electrolyte body;

said heater element having holes adjacent a second end, and having means for electric contact to said heating resistor; and a plurality of electrical connection terminals each having a connecting end for electrical connection to an external signal, a contact end for electrically contacting said means for electric contact to the resistor, and a male portion extending into one of said holes in said heater element to rigidly secure said heater and to prevent rotational movement of the heater element.

2. A device as set forth in claim 1 further comprising an electrically insulative adapter having a generally tubular shape positioned to enclose said electrical connection terminals.

* * * * *